(12) United States Patent
Hashimoto et al.

(10) Patent No.: US 9,090,672 B2
(45) Date of Patent: Jul. 28, 2015

(54) METHOD FOR PRODUCING ANTIBODY DIRECTED AGAINST PROTEIN EXPRESSED ON CELL SURFACE

(75) Inventors: Shu-ichi Hashimoto, Tokyo (JP); Donghui Li, Tokyo (JP); Shoko Ishida, Tokyo (JP); Hidetaka Seo, Tokyo (JP); Chika Koyama, Tokyo (JP); Yukiko Banzai, Tokyo (JP); Naoto Harigai, Tokyo (JP); Isao Kohno, Tokyo (JP)

(73) Assignee: CHIOME BIOSCIENCE INC., Tokyo (JP)

( * ) Notice: Subject to any disclaimer, the term of this patent is extended or adjusted under 35 U.S.C. 154(b) by 483 days.

(21) Appl. No.: 13/132,462

(22) PCT Filed: Dec. 7, 2009

(86) PCT No.: PCT/JP2009/006657
§ 371 (c)(1),
(2), (4) Date: Aug. 12, 2011

(87) PCT Pub. No.: WO2010/064454
PCT Pub. Date: Jun. 10, 2010

(65) Prior Publication Data
US 2011/0306126 A1    Dec. 15, 2011

(30) Foreign Application Priority Data
Dec. 5, 2008   (JP) .................. 2008-311021

(51) Int. Cl.
*C40B 30/06* (2006.01)
*C07K 16/00* (2006.01)
*C07K 16/28* (2006.01)

(52) U.S. Cl.
CPC ............ *C07K 16/00* (2013.01); *C07K 16/28* (2013.01); *C07K 16/2863* (2013.01); *C07K 2317/10* (2013.01); *C40B 30/06* (2013.01)

(58) Field of Classification Search
None
See application file for complete search history.

(56) References Cited

U.S. PATENT DOCUMENTS
2006/0275288 A1   12/2006  Grihalde et al.

FOREIGN PATENT DOCUMENTS

| GB | 2408332 | 5/2005 |
|----|---------|--------|
| JP | 2005168437 | 6/2005 |
| JP | 2005185281 | 7/2005 |

OTHER PUBLICATIONS

Seo et al. (Apr. 15, 2007) Biotechnology and Genetic Engineering Reviews vol. 24 pp. 179 to 194.*
Zacchi et al. (1998) The Journal of Cell Biology vol. 140 pp. 1039 to 1053.*
Dalerba et al. (Jun. 4, 2007) PNAS USA vol. 104 pp. 10158 to 10163 including supporting information.*

(Continued)

*Primary Examiner* — Christian Boesen
(74) *Attorney, Agent, or Firm* — Pearne & Gordon LLP (57) ABSTRACT

Disclosed is a method for producing an antibody directed against a protein, particularly a transmembrane protein, expressed on the surfaces of cells.
Specifically disclosed is a means for obtaining a desired antibody by mixing cells capable of expressing an antigen protein on the surfaces thereof (i.e., antigen molecule-expressing cells) with an antibody library composed of antibody-expressing cells, viruses or the like, and subsequently concentrating/isolating only components (e.g., antibody-expressing cells, viruses) capable of binding to the antigen molecule-expressing cells from the components (e.g., antibody-expressing cells, viruses) of the antibody library.

15 Claims, 5 Drawing Sheets

(56) References Cited

OTHER PUBLICATIONS

Todo K. et al, Novel in vitro screening systems for monoclonal antibodies using hypermutating chicken B cell library, Journal of Bioscience and Bioengineering, Elsevier, Amsterdam, NL, vol. 102, No. 5, Nov. 1, 2006, pp. 478-481.
Hoogenboom, H.R. et al, Selection-Dominant and nonaccessible epitopes on cell-surface receptors revealed by cell-panning with a large phage antibody library, European Journal of Biochemistry, Blackwell Publishing, Berlin, DE, vol. 260, No. 3, Mar. 1, 1999, pp. 774-784.
Kupsch, J.M. et al, Isolation of human tumor-specific antibodies by selection of an antibody phage library on melanoma cells, Clinical Cancer Research, The American Association for Cancer Research, US, vol. 5, No. 4, Apr. 1, 1999, pp. 925-931.
Peipp, M. et al, An improved procedure for the generation of recombinant single-chain Fv antibody fragments reacting with human CD13 on intact cells, Journal of Immunological Methods, Elsevier Science Publishers B.V., Amsterdam, NL, vol. 251, No. 1-2, May 1, 2001, pp. 161-176.
Yuan, Qing-An et al, Isolation of anti-MISIIR scFv molecules from a phage display library by cell sorter biopanning, Cancer Immunology Immunotherapy, vol. 57, No. 3, Mar. 2008, pp. 367-378.
Supplementary European Search Report dated Jan. 24, 2013 for related application No. EP09830224.
Seo, et al., "Rapid generation of specific antibodies by enhanced homologous recombination", Nature Biotechnology, vol. 23, No. 6, 731-735, Jun. 2005.
Marks, et al., "By-passing Immunization Human Antibodies from V-gene Libraries Displayed on Phage", J. Mol. Biol. (1991) 222, 581-597.
Tang et al., "Genetic immunization is a simple method for eliciting an immune response", Nature, vol. 356, 152, Mar. 12, 1992.
McCafferty et al., "Phage antibodies: filamentous phage displaying antibody variable domains", Nature, vol. 348, 552-554, Dec. 6, 1990.
International Search Report for International Application No. PCT/JP2009/006657, completed on Jan. 5, 2010 and mailed on Jan. 19, 2010.
Office action dated May 27, 2013 in corresponding patent application No. 200980154881X in China.
European Patent Office Report dated Feb. 19, 2014 for Application No. 09-830-224.3-1412.
Office action dated May 12, 2014 in corresponding Japanese patent application No. 2010-541252.

\* cited by examiner

METHOD FOR PRODUCING ANTIBODY DIRECTED AGAINST PROTEIN EXPRESSED ON CELL SURFACE

TECHNICAL FIELD

The present invention relates to a method for isolating an antibody directed against a protein expressed on a cell surface, and an antibody produced by the above-described method.

BACKGROUND ART

Antibodies recognize specific antigens and thereby provoke various in vivo phenomena. Thus, antibodies play an important role in in vivo defense mechanisms. In particular, since antibodies have antibody dependent cell-mediated cytotoxicity (ADCC) and complement dependent cytotoxicity (CDC), which are effective for elimination of cancer cells and the like, they have been used as anticancer agents. There are many antibody agents, which have been produced as a result of focusing the above-mentioned activities and have been put into practical use. Among such antibody agents, a considerable number of agents exhibit good therapeutic effects. In addition to the intended use as pharmaceutical agents, antibodies have been widely used as, for example, various diagnostic agents, or useful tools for research and development. Accordingly, it is desired to produce an antibody which recognizes, as an antigen, a protein that plays an important role in various in vivo phenomena.

An example of such a protein that plays an important role in in vivo phenomena is a protein that penetrates to a cell membrane (hereinafter referred to as a "transmembrane protein"). Examples of such a transmembrane protein include various types of receptor proteins and ion channel proteins. A majority of such transmembrane proteins are associated with transmission and/or migration of information and substances inside and outside a cell, and thereby they play an important role in the survival, growth, differentiation and the like of the cell. Thus, it is extremely significant to produce an antibody capable of recognizing the above-described transmembrane protein, which can be used as the aforementioned pharmaceutical agent, diagnostic agent, or research and development tool.

To date, there have been developed various methods for producing an antibody directed against any given antigen (a hybridoma production method, a DNA immunization method, a phage display method, etc.). Particularly, in recent years, a method, referred to as an ADLib system (or an ADLib method), has attracted considerable attention as a technique of easily producing a large amount of antibody having high specificity (see Patent Literature 1 and Non Patent Literature 1). According to this method, an antibody having desired specificity and affinity can be provided by a simple method.

However, the production of an antibody directed against a transmembrane protein according to the above-described various methods for producing antibodies has been problematic in the following respects.

In the method of directly administering a transmembrane protein-expressing cell as an antigen to an animal to be immunized, so as to induce an immune response, the transmembrane protein is expressed in a physiologically three-dimensional structure on the protein-expressing cell membrane. Since the protein-expressing cell undergoes protein degradation in vivo, it is difficult to produce an antibody directed against the transmembrane protein that is in a physiological state.

The DNA immunization method comprises incorporating the cDNA of a transmembrane protein into a suitable mammalian cell expression vector and then directly administering the expression vector to an animal to be immunized (see Non Patent Literature 2). According to this method, the three-dimensional structure of the transmembrane protein is likely to be reproduced on a cell membrane in vivo. However, the action mechanism of the protein is still unknown, and thus, whether or not an antibody can be produced directed against the transmembrane protein that is in a physiological state has not yet been clarified.

The phage display method is a system whereby an antibody variable region gene is fused with a coat protein of a filamentous phage as one type of *Escherichia coli* virus, such that the infectious ability of the phage is not lost, and the gene is allowed to express as a fusion protein (see Non Patent Literatures 3 and 4). In this method, when phage particles are allowed to react with a transmembrane protein and a desired antibody is selected, the use of a purified transmembrane protein is required, and whether or not the transmembrane protein as a target maintains physiological functions is not guaranteed.

The ADLib method, which promotes somatic homologous recombination that occurs in immunocytes so that a variety of antibody molecules are presented on the surfaces of the immunocytes, also has the above-described problems. Hence, it is not always easy to select an antibody directed against a transmembrane protein which is hardly purified in a physiological state.

Given the above, it has been difficult for all of the production methods to produce an antibody directed against a transmembrane protein.

CITATION LIST

[Patent Literature 1] International Publication WO2004/011644
[Non Patent Literature 1] Seo et al., Nature Biotech. 23: 731-735, 2005
[Non Patent Literature 2] Tang et al., Nature 356: 152, 1992
[Non Patent Literature 3] McCafferty et al., Nature 348: 552-554, 1990
[Non Patent Literature 4] Marks et al., J. Mol. Biol. 222: 581-597, 1991

SUMMARY OF INVENTION

Technical Problem

Under the aforementioned circumstances, the present inventors have conducted intensive studies. As a result, the inventors have succeeded in preparing an antibody directed against a transmembrane protein from an antibody population, using cells that express a transmembrane protein and a marker protein on the surfaces thereof.

Thus, it is an object of the present invention to provide a method for producing an antibody directed against a protein that is expressed on a cell surface, and particularly, a transmembrane protein.

Solution to Problem

Upon production of an antibody directed against a transmembrane protein, the present inventors prepared cells that express a transmembrane protein and a marker protein on the surfaces thereof, instead of magnetic beads coated with purified antigens, which had been used in conventional antibody production methods involving the ADLib method. Using the prepared cells as antigens, the inventors screened for an antibody-presenting cell from an ADLib library. Thereafter, using a molecule specifically binding to the marker protein, the inventors isolated a complex consisting of the aforementioned cell and the antigen-presenting cell. Only by such means, whether or not a specific antibody directed against a transmembrane protein that is in a physiological state can be precisely selected was unknown. As a result of analysis, however, it was confirmed that an antibody having effective specificity and affinity can be unexpectedly obtained by the above-described method. According to this method, it becomes possible to produce an antibody directed against a transmembrane, which has been hardly produced by conventional methods. By presenting the transmembrane protein in a physiological state, the probability of obtaining a functional antibody that has effects on the functions of the transmembrane protein can be enhanced. In addition, this method is also advantageous in that, by allowing cells to express any given transmembrane proteins, all types of transmembrane proteins can be screened without purification.

Specifically, the present invention relates to the following (1) to (6):

(1) A first aspect of the present invention relates to "a method, which comprises allowing an antibody library to come into contact with cells that express a target antigen protein on the surfaces thereof and isolating the cells, so as to separate a constituent member of the antibody library that forms a complex with the target protein."

(2) A second aspect of the present invention relates to "the method according to (1) above, wherein the antibody library is a cell population comprising cells that present an antibody on the surfaces thereof"

(3) A third aspect of the present invention relates to "the method according to (1) above, wherein the method of isolating the cells that express a target antigen protein on the surfaces thereof utilizes the bond between a marker antigen that is present on the cell surface, other than the target antigen protein expressed on the cell surface, and an antibody directed against the marker antigen."

(4) A fourth aspect of the present invention relates to "the method according to (3) above, wherein the marker antigen is a foreign protein."

(5) A fifth aspect of the present invention relates to "the method according to (4) above, wherein the target antigen protein is a foreign protein."

(6) A sixth aspect of the present invention relates to "the method according to any one of (2) to (5) above, wherein the cell population comprising cells that present an antibody on the surfaces thereof is DT40."

Advantageous Effects of Invention

In the present invention, an expression vector, into which any given protein expressed on a cell membrane, and particularly, a transmembrane protein gene has been incorporated, is used, and the protein acting as an antigen is expressed on the surface of any given cell (antigen molecule-expressing cell). Then, the cell is mixed with a certain type of antibody library including, as typical examples, antibody-expressing cells used in the ADLib method. Thereafter, from among antibody-expressing cells, viruses and the like, which constitute the aforementioned antibody library, only those that bind to the antigen molecule-expressing cells are concentrated and isolated, thereby enabling production of an antibody.

When compared with the conventional antibody production methods, the method of the present invention does not require purification of an antigen protein. Accordingly, even in the case of a multiple transmembrane protein, which is hardly purified, an antibody can be produced. Moreover, by presenting the transmembrane protein in a physiological condition, it is possible not only to recognize the transmembrane protein, but also to enhance the probability of obtaining what is called a functional antibody that has effects on the functions of the transmembrane protein.

BEST MODE FOR CARRYING OUT THE INVENTION

1. Antibody Library

The antibody library used in the present invention is not particularly limited, as long as it includes a group of antibodies. Thus, the present antibody library may be either cells that present antibodies on the surfaces thereof, or viruses that present antibodies conjugated to the virus coat proteins. A person skilled in the art could readily select a suitable library. As such an antibody library, B cells that produce antibodies are preferably used, and DT40 cells that are the established cultured cells of chicken-derived B cells are particularly preferable. An antibody library produced by the ADLib method is particularly preferable (for details of the ADLib method, see Patent Literature 1, for example).

The antibody library used in the present invention is maintained by a method well known in the present technical field. Needless to say, the selected antibody library is maintained under conditions suitable therefor. When the selected antibody library consists of a DT40 cell population, IMDM medium (Invitrogen) is used as a medium for maintaining the cell population, and the cells are cultured at 39.5° C. in the presence of 5% $CO_2$, for example.

The above-described DT40 cells include cells, on which a treatment for promoting somatic homologous recombination so as to present a variety of antibody molecules on the surfaces thereof has been performed. The methods for promoting somatic homologous recombination include a method that could readily be selected by a person skilled in the art. An example of the methods for promoting somatic homologous recombination is a method of alleviating a chromatin structure at the antibody gene locus of the DT40 cells, for example, by allowing the cells to come into contact with a histone deacetylase inhibitor such as Trichostatin A, so as to promote somatic homologous recombination at the antibody gene locus. A specific example of such a method is the ADLib method.

2. Antigen Protein and Marker Antigen

Upon the implementation of the present invention, the antigen protein of interest is not particularly limited, as long as it is a protein that is presented on the surface of a cell, after it has been expressed in the cell. The antigen protein of interest may be either an antigen protein originally existing in a cell, or a foreign antigen protein. Preferred examples of such an antigen protein include: proteins that penetrate to a cell membrane, including growth factor receptor proteins, such as EGFR and IGF-1R; four-transmembrane proteins such as CD81; and seven-transmembrane proteins including chemokine receptors such as CXCR4 and sphingolipid receptors.

The marker antigen used to isolate a complex of an antigen protein and an antibody (or a cell that presents the antibody), after the cell has bound to the above-described antibody library, is not particularly limited, as long as it is a molecule serving as a so-called "tag" for specifically recognizing an antigen protein-expressing cell. Examples of the molecule that can be used as a marker antigen include molecules existing on the cell membrane, such as a protein and a sugar chain. The present molecule may be either a molecule originally exiting on the cell membrane, or a foreign molecule that has not originally existed in the cell. The marker antigen originally existing on the cell membrane does not need to be necessarily identified as a molecule, as long as it can be used to recognize an antigen protein-expressing cell. For instance, if (a group of) antibodies could be obtained with respect to a group of biomolecules existing on the surface of a cell that expresses an antigen protein, the antigen protein can be recognized or selected using these antibodies. Thus, the identity of the group of biomolecules need not be disclosed. When a foreign molecule is used as a marker antigen, a protein expressed on a cell surface may be used, for example. When a foreign protein is used as a marker antigen, the type of the used protein is not limited, as long as it is presented on the surface of a cell after it has been expressed in the cell. Not only a membrane protein expressed on the surface of a cell membrane, but also a molecule that is not originally presented on a membrane, such as a secretory protein, may be used as a marker antigen, after it has been fused with a transmembrane region. Examples of the marker antigen that can be used herein include CD4 and an MHC class 2 molecule.

The genes of the above-described antigen protein and marker protein (in the case of using a protein as a marker antigen) can be prepared based on common technical knowledge in the present technical field. For example, the gene regions of the antigen protein and marker protein of interest may be amplified from suitable cells, etc., according to an RT-PCR method or the like, and thereafter, the amplified products may be each cloned into a suitable vector. When the marker protein is a fusion protein, genes encoding individual proteins to be fused may be amplified by the same method, and the amplified products may be then cloned into a suitable vector, separately or in a fused state. In this case, primers used in the RT-PCR method may be easily designed by obtaining sequence information from known database regarding the genes of the antigen protein and marker protein of interest (in the case of a fusion protein, individual proteins to be fused), and then using the obtained information.

3. Cell that Co-Expresses Antigen Protein and Marker Protein

Upon the implementation of the present invention, when a protein is used as a marker, the type of a cell that co-expresses the above-described antigen protein and marker protein is not particularly limited, as long as it is a cell capable of presenting these proteins on the surface thereof, after the proteins have been expressed therein. A person skilled in the art could readily select such a cell. In particular, when the antigen protein and the marker protein are derived from a human, preferred examples of the above-described co-expressing cells include: human-derived cells in which physiological post-translational modification or intracellular localization is likely to be provoked; and easily handled, established cultured cells (for example, CHO-S cells).

The produced antigen protein gene and marker protein gene are incorporated into a suitable expression vector, so that a desired antigen protein and a desired marker protein can be expressed in the above-described cells. When a fusion protein is used as a marker protein, the frame of each gene is adjusted and is then expressed, so that a desired fusion protein having an amino acid sequence of interest can be expressed. As an expression vector, there is preferably used a vector comprising constitutional elements, such as a promoter and an enhancer, which is capable of expressing a protein of interest in the cell.

The produced expression vector can be easily introduced into the above-described cell according to a known method such as a DEAE dextran method, an electroporation method, a calcium phosphate method or a method using cationic lipids.

4. Selection of Desired Library Constituent Members from Antibody Library with Use of Antigen Protein and Marker Protein Co-Expressing Cells Upon the implementation of the present invention, cells that co-express the above-described antigen protein and marker protein are suspended in and mixed with an antibody library under suitable conditions (for example, at physiological ionic strength and pH), and the obtained mixture is then incubated at an appropriate temperature (for example, approximately 4° C. to 37° C.) for an appropriate period of time (for example, 1 hour to overnight), so as to carry out a binding reaction between the co-expressing cells and an antibody library constituent member (e.g. antibody-expressing cells) in the antibody library, which corresponds to a specific antibody having specificity to the antigen protein.

After completion of the binding reaction, a binding body of the co-expressing cells and the antibody library constituent member is isolated by a suitable method using a marker. During this isolation operation, a method that is non-invasive to the antibody library constituent member to be recovered, such as antibody-expressing cells, is preferably applied. Such invasive method includes all methods that could readily be selected by a person skilled in the art. When the marker is a biomolecule such as a protein or a sugar chain, for example, magnetic beads coated with specific antibodies directed against such biomolecules, such as MACS beads (Miltenyi Biotech) or Dynabeads (Veritas) are used. Such beads are mixed with the binding body under suitable conditions, and the binding body can be then isolated by an MACS method or a Dynabeads stand method. In addition, when Dynabeads are used, the binding body can also be isolated using a King-Fisher Magnetic Particle Processor (Thermo Fisher Scientific).

Examples will be given below. However, these examples are not intended to limit the scope of the present invention.

Examples

1. Cell Culture

The culture of DT40 cells was basically carried out according to the following method. Using a $CO_2$ thermostatic chamber as an incubator, the cells were cultured at 39.5° C. in the presence of 5% $CO_2$. IMDM medium (Invitrogen) was used as a medium. To the medium, 10% bovine serum, 1% chicken serum, 100 U/mL penicillin, 100 μg/mL streptomycin, and 55 μM 2-mercaptoethanol were added, and the obtained medium was then used. Trichostatin A (Wako Pure Chemical Industries, Ltd.) dissolved in a concentration of 2 mg/mL in DMSO was used as a stock. This stock was diluted with a medium, as appropriate, resulting in a final concentration of 1.25 ng/ML or 2.5 ng/ML, and was then used.

The culture of CHO-S cells was basically carried out according to the following method. Using a $CO_2$ thermostatic chamber as an incubator, the cells were cultured at 37° C. in the presence of 5% $CO_2$. As a medium, CHO-S SFM medium (Invitrogen) was used.

An EGFR #36 clone was isolated as a clone for producing anti-EGFR IgM by selection involving the ADLib system, using an EGFR-Fc recombinant protein (R & D Systems).

An ADLib system library was maintained by adding Trichostatin A (Wako Pure Chemical Industries, Ltd.) to the medium every day so as to result in a final concentration of 1.25 ng/mL or 2.5 ng/mL. From the day before use, the library was cultured in a medium that did not contain Trichostatin A.

2. Transfection of CHO-S Cells with EGFR and CD4 Genes

An EGFR expression vector was produced by the following procedures of PCR using Pyrobest Polymerase (Takara Bio, INC.). A Human EGFR cDNA clone (Open Biosystems; Clone ID 30528231; Accession No. BC094761) was used as a template, and full-length cDNA was amplified using NheI_EGFR—F and hEGFR cDNA-3' (BC094761) as primers. The reaction conditions were as follows. That is, the reaction was carried out at 95° C. for 30 seconds, 30 cycles of: 95° C., 30 seconds; 58° C., 30 seconds; and 72° C., 3 minutes, and then at 72° C. for 8 minutes. Thereafter, ExTaq (Takara Bio, INC.) was added to the thus obtained Human EGFR cDNA, and the obtained mixture was then reacted at 72° C. for 15 minutes, so as to add "A" to the Human EGFR cDNA. Using a DH5α strain (Takara Bio, INC.), the reaction product was subcloned into a pGEM-T easy vector (Promega) (clone 1). Since this clone 1 lacked exon 4, total RNA was extracted from A431 cells using QuickGene RNA cultured cell kit S (Fujifilm Corporation), and it was then subjected to a reverse transcription reaction at 50° C. for 50 minutes and at 85° C. for 5 minutes, using Superscript III first strand synthesis system (Invitrogen). Using the obtained first strand cDNA as a template, cDNA was synthesized by PCR, and it was then subcloned into a pGEM-T easy vector. As primers, NheI_EGFR—F and EGFR—R(NM_005228) were used.

This clone (clone 2) comprised Exon 4, but it had a large number of mutations on other sequences. Thus, the Exon 4 of clone 2 was inserted into clone 1 by PCR. An Exon 4 fragment was synthesized from clone 2, using hEGFR_ex4-5' and hEGFR_ex4-3' as primers. The synthesized Exon 4 fragment was mixed with clone 1, and the obtained mixture was used as a template. PCR was carried out using, as primers, NheI_EGFR—F and hEGFR_ex4-3' (used in the synthesis of clone 1.1), and hEGFR_ex4-5' and hEGFR cDNA-3' (BC094761) (used in the synthesis of clone 1.2). The obtained PCR products (clone 1.1 and clone 1.2) were mixed with each other. Using the thus obtained mixture as a template, PCR was carried out with NheI_EGFR—F and hEGFR cDNA-3' (BC094761) as primers. The obtained PCR product was subcloned into a pGEM-T easy vector (Promega) (clone 3). The sequence was determined using ABI PRISM 377 Sequencer of ABI.

Clone 3 was cleaved by HindIII, was then blunt-ended using a Klenow fragment (Takara Bio, INC.), and was further cleaved by NheI, so as to obtain an insert fragment. Likewise, pIRESpuro3 (Takara Bio, INC.) was cleaved by EcoRI, was then blunt-ended, and was then cleaved by NheI, so as to obtain a vector fragment. Both the vector fragment and the insert fragment were purified using Qiaquick GelExtraction Kit (Qiagen), and they were then ligated to each other, using Ligation Convenience Kit (Nippon Gene Co., Ltd.). Thereafter, a DH5α strain was transformed with the ligate, so as to obtain a pIRESpuro3 EGFR expression vector.

```
(Primer sequences)
NheI_EGFR-F:
TTGCTAGCCCAGTATTGATCGGGAGAGC       (SEQ ID NO: 1)

hEGFR cDNA-3' (BC094761):
CAGGCTCGGTCATGTGTTTA               (SEQ ID NO: 2)

EGFR-R (NM_005228):
GCACCTGTAAAATGCCCTGT               (SEQ ID NO: 3)

hEGFR_ex4-5':
GCCCATGAGAAATTTACAGGAAATC          (SEQ ID NO: 4)

hEGFR_ex4-3':
CAGCTTGGATCACACTTTTGGCA            (SEQ ID NO: 5)

hEGFR_ex4-5':
GCCCATGAGAAATTTACAGGAAATC          (SEQ ID NO: 6)

hEGFR_ex4-3':
CAGCTTGGATCACACTTTTGGCA            (SEQ ID NO: 7)
```

As an expression vector for CD4, a pMACS 4.1 plasmid in MAC select transfected cell selection kit manufactured by Miltenyi Biotech was used.

Transfection was basically carried out using Cell Line Nucleofector Kit V (Amaxa Biosystems) in accordance with protocols included with the kit. $1 \times 10^6$ cells were recovered and were then suspended in 100 μL of PBS. To the suspension, pIRESpuro3 EGFR and pMACS4.1 (1 μg each) were added, and transfection was then carried out using program U-024. Thereafter, the cells were recovered and were then cultured in a CHO-S-SFM medium for 16 hours.

3. Selection of Anti-EGFR Antibody-Expressing Cells from Adlib Library with Use of CHO-S Cells that Co-Express EGFR and CD4

3-1. Binding of CHO-S Cells that Express EGFR and CD4 to Anti-EGFR Antibody-Expressing Cells in ADLib Library EGFR- and CD4-expressing CHO-S cells and ADLib library cells ($1 \times 10^8$ cells) were suspended in DMEM (Invitrogen) that contained 2% bovine serum (Invitrogen), and the cells were then mixed. While shaking, the obtained mixture was incubated at 4° C. for 1 hour, so that a binding reaction was carried out between the EGFR— and CD4-expressing CHO-S cells and the anti-EGFR antibody-expressing cells in the ADLib library. Thereafter, the thus incubated cells were recovered by centrifugation at 120×g for 5 minutes, and they were then suspended in an MACS buffer (Miltenyi Biotech) containing 10% chicken serum.

3-2. Concentration of Binding Body of Anti-EGFR-Expressing DT40 Cells and EGFR and CD4 Co-Expressing CHO Cells by MACS Operations were basically carried out in accordance with the protocols of Miltenyi Biotech. That is, 200 µL of anti-CD4 microbeads were added to the cells that had been suspended in the MACS buffer as described above, and they were then mixed. Thereafter, the obtained mixture was left at rest on ice for 15 minutes. An LS column (Miltenyi Biotech) was first equilibrated with 3 mL of an MACS buffer containing 10% chicken serum. Subsequently, 1 mL of an MACS buffer containing 10% chicken serum was added to the above mixture of the cells and the microbeads to a total amount of 2 mL. The obtained solution was applied to the column. To the column, 5 mL of an MACS buffer containing 10% chicken serum was applied three times, so that cells that had non-specifically bound to the column were washed out. Thereafter, the column was removed from the magnetic stand, and cells that had bound to the CD4 microbeads were recovered using 5 mL of an MACS buffer that did not contain 10% chicken serum. This operation was repeated twice. The recovered cells were cultured overnight in a medium used in the aforementioned culture of DT40 cells.

Figure 1:
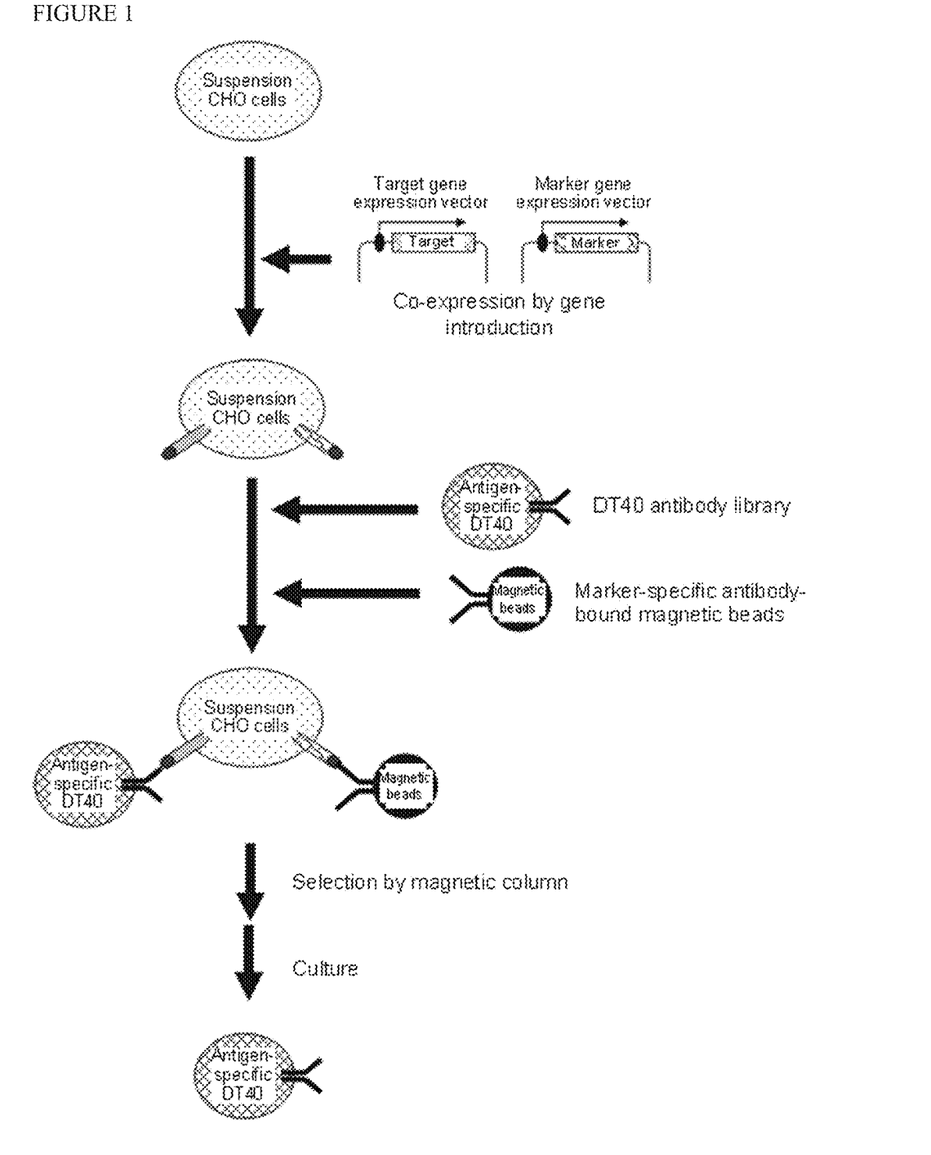
FIG. 1 shows a flow of ADLib selection using a membrane protein expressed on a cell surface.
Figure 2:
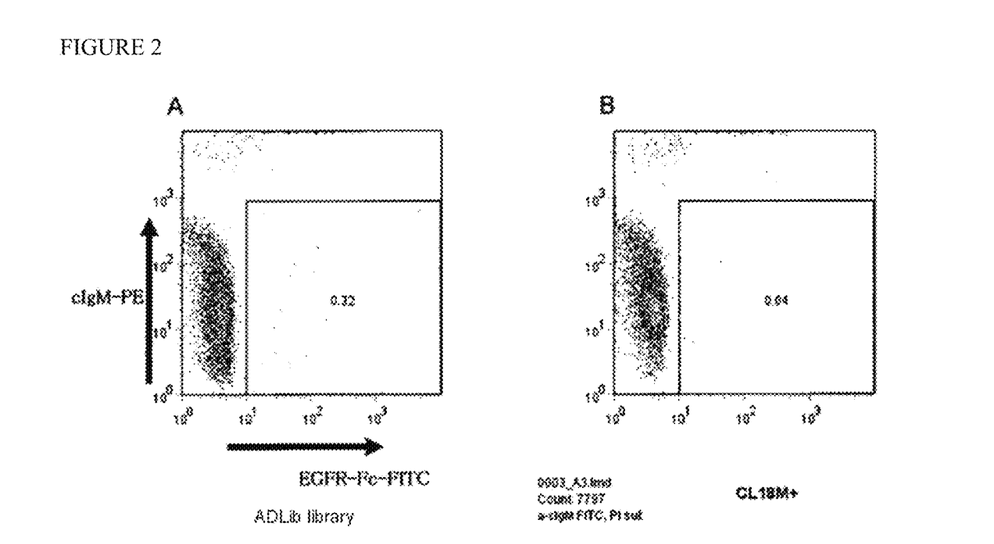
FIG. 2 shows the results obtained by FACS analysis to determine the ratio of cells that express both chicken IgM and an anti-human EGFR antibody, to ADLib library constituent cells which have been selected using human EGFR and CD4 co-expressing CHO-S cells, and negative control cells.

3-3. Confirmation by FACS Analysis of Concentration of Binding Body of Anti-EGFR-Expressing DT40 Cells and EGFR and CD4 Co-Expressing CHO Cells The $5 \times 10^5$ cells that had been cultured overnight in the above section 3-2 were recovered by centrifugation at 1,100 g at 4° C. for 5 minutes, and they were then washed once with an FACS buffer (a phosphate buffered saline containing 0.3% bovine serum albumin) Thereafter, the cells were suspended in an EGFR-Fc protein (R & D Systems; dissolved in a concentration of 0.2 µg/mL in a phosphate buffered saline, and then used), and were then left at rest on ice for 20 minutes. During this operation, tapping was carried out every 10 minutes, so that the re-suspension of the cells was promoted. The cells were recovered in the same manner as described above, and were then washed with an FACS buffer twice. Thereafter, the cells were suspended in an FITC-conjugated anti-human IgG antibody (eBioscience; used at 200-fold dilution) and PE-conjugated anti-chicken IgM antibody (Beckmann Coulter; used at 200-fold dilution), and were then left at rest on ice for 20 minutes. During this operation, tapping was carried out every 10 minutes, so that the re-suspension of the cells was promoted. The cells were recovered in the same manner as described above, and were then washed with an FACS buffer twice. Thereafter, the cells were suspended in 400 µL of an FACS buffer containing 1 µg/mL propidium iodide, and were then subjected to FACS analysis, so as to obtain the ratio of cells to which both FITC and PE showed positive (namely, cells that express both chicken IgM and an anti-EGFR antibody). For the FACS analysis, Cell Lab Quanta SP MPL (Beckmann Coulter) was used, and as analysis software, Flowjo (Tree Star) was used. FIG. 2 shows an example of the results of this experiment. FIG. 2B shows the results of the same experiment which was performed on a cell population containing no DT40 clones reacting with EGFR. Concentration of EGFR-specific cells, which is shown in the square, is not observed at all. In contrast, in FIG. 2A showing the results of an experiment using ADLib library cells, concentration of the cells (0.32%) is observed in the square. These results show that this experiment was carried out in a correct manner.

Figure 3:
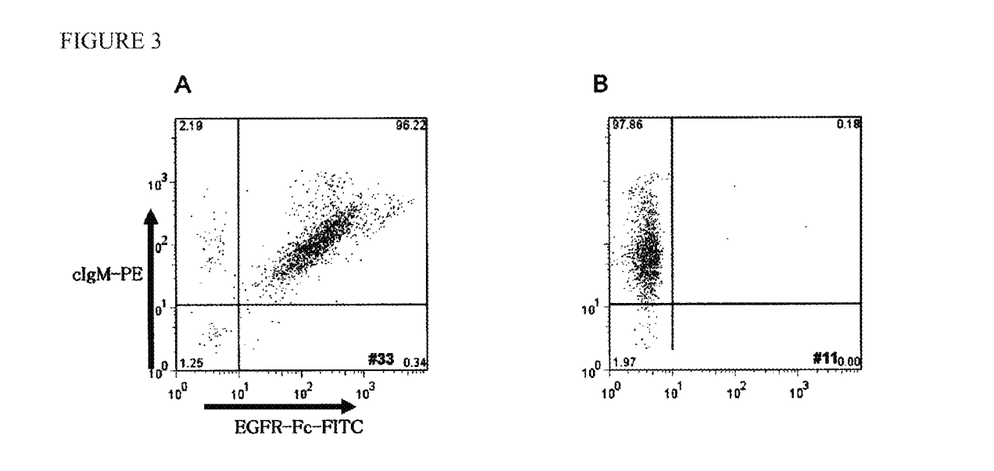
FIG. 3 shows the results obtained by FACS analysis of the ratio of cells that express both chicken IgM and an anti-human EGFR antibody, to anti-human EGFR antibody-producing cells and anti-human EGFR antibody non-producing cells, which have been screened from an ADLib library.

4. FACS Sorting of Anti-Chicken IgM Antibody- and EGFR-Fc Chimera-Positive Cells, and FACS Analysis of Isolated Cells From among the cells recovered from the library, a cell group (a portion enclosed with the square in FIG. 2A), to which both an anti-chicken IgM antibody and an EGFR-Fc protein gave positive signals, was subjected to FACS sorting. As a sorter, EPICS Elite ESP of Beckmann Coulter was used. The cells found in the square in FIG. 2 were placed to a 96-well plate (Nunc) filled with a medium used for DT40. The cells were cultured for approximately 1 week, so as to form single cell-derived colonies. As a result, 55 colonies were recovered. Expression of an anti-EGFR antibody in these colonies was confirmed by FACS analysis. Staining and analysis were carried out in accordance with the methods described in the section 3-2 above. Consequently, staining with EGFR-Fc chimera was observed in 53 out of the 55 clones, and thus, it was confirmed that the clones were able to produce an antibody directed against EGFR. One (clone #33) out of these clones is shown in FIG. 3A. Production of anti-EGFR was not observed in 2 out of the 55 clones. The one clone (clone #11) that did not produce anti-EGFR is shown in FIG. 3B.

5. ELISA Analysis for Analyzing Specificity of Isolated Clones

ELISA was carried out as follows.

First, with regard to the 55 clones isolated in the section 4 above, $1 \times 10^6$ cells for each clone were cultured in a medium for DT40 that did not contain chicken serum for 2 days, so as to produce IgM. Thereafter, the culture supernatant was recovered. The concentration of IgM in the culture supernatant was measured using Chicken IgM ELISA Quantification Kit (BETHYL) in accordance with protocols included therewith. ELISA analysis was carried out in an IgM concentration of 1 µg/mL for each clone.

Figure 4:
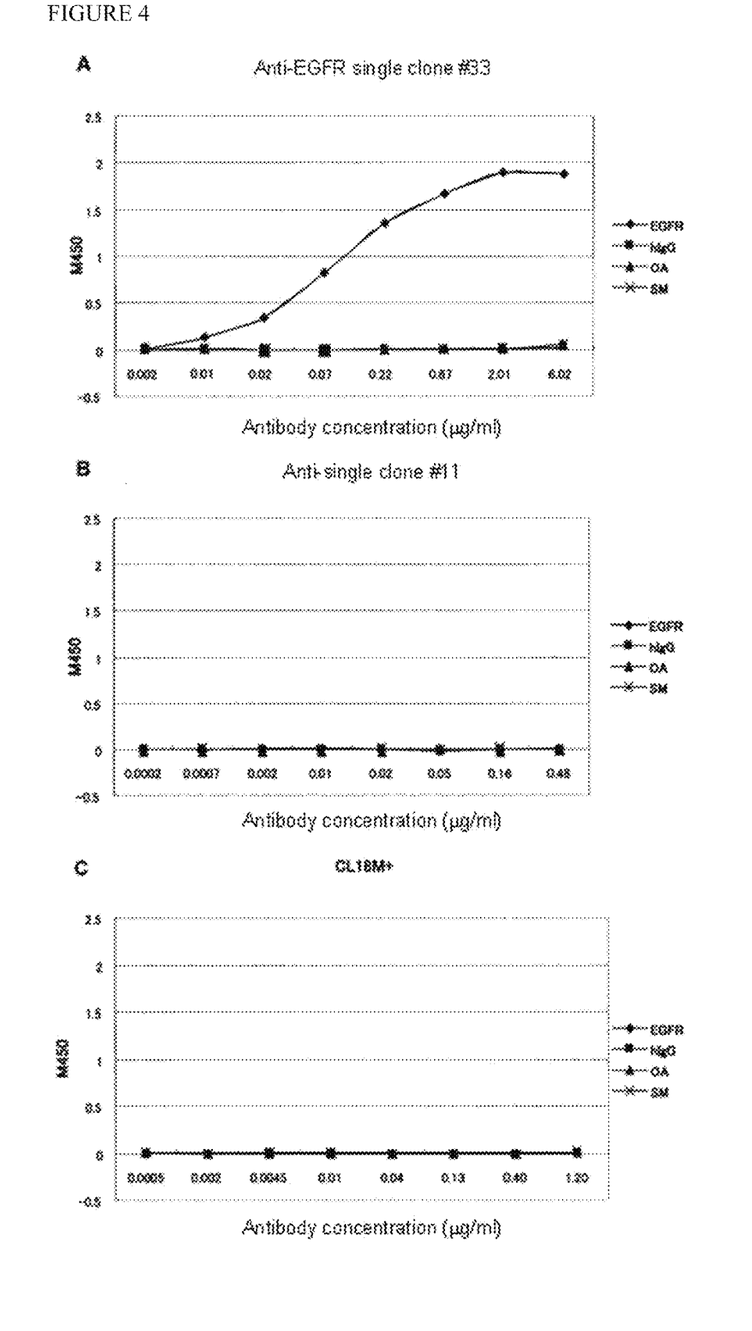
FIG. 4 shows the results of ELISA, which show the antigen specificity of antibodies produced by anti-human EGFR antibody-producing cells.

100 µL each of 1 µg/mL EGFR-Fc was dispensed into a 96-well immunoplate, U-96 Maxisorp (Nunc), and it was then incubated overnight. As a control to be used to analyze the specificity of an antibody, human IgG BSA was also immobilized on a plate. On the following day, the content in the plate was discarded, and 200 µL of a blocking buffer (PBS containing 0.5% skimmed milk) was added to the plate, followed by incubation at room temperature for 2 hours. Thereafter, the reaction solution was washed with 200 µL of an ELISA washing buffer (PBS containing 0.05% Tween 20) three times. 100 µL of the 53 anti-EGFR-expressing candidate clones and 100 µL of a CL18 clone-derived culture supernatant were each added to the resultant, and the obtained mixture was then incubated at room temperature for 1 hour. The reaction solution was washed with 200 µL of an ELISA washing buffer five times, and 100 µL of a secondary antibody (anti-chicken IgM-HRP; BETHYL) that had been 5000-fold diluted with PBS was then added to the resultant. The obtained mixture was incubated at room temperature for 45 minutes. As such a secondary antibody, anti-chicken IgM-HRP (BETHYL) was used. The reaction solution was washed with 200 µL of an ELISA washing buffer five times, and 100 µL of TMB+(Dako) was then added to the resultant, followed by incubation for 10 minutes. Thereafter, the reaction was terminated by addition of 100 µL of 1 N sulfuric acid, the absorbance at 450 nm was then measured, and the number of clones producing an antibody specific to EGFR and their reference numbers were then analyzed. The results of clone #33, clone #11 and non-specific clone (CL18M+) are shown in FIGS. 4A, 4B and 4C, respectively. From these results, it became clear that the antibody produced by clone #33 is specific to EGFR. The same results were also obtained from the 52 other clones that were specific to EGFR.

6. FACS Analysis for Analyzing Specificity of Isolated Clones

In order to further analyze the specificity of the isolated clones, FACS analysis was carried out using squamous cell carcinoma cell line A431, which has been known to express EGFR at a high level.

The culture of A431 cells was basically carried out by the following method. Using a $CO_2$ thermostatic chamber as an incubator, the cells were cultured at 37° C. in the presence of 5% $CO_2$. DMEM medium (Invitrogen) was used as a medium. To the medium, 10% bovine serum, 100 U/mL penicillin, and 100 μg/mL streptomycin were added, and the obtained medium was then used.

Figure 5:
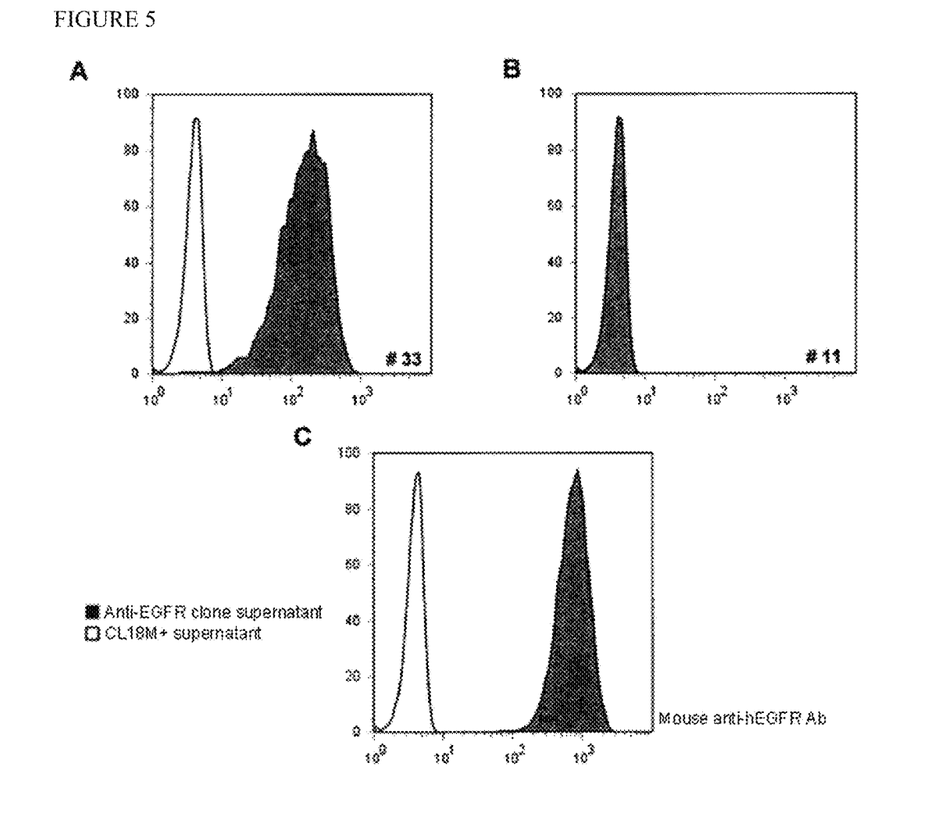
FIG. 5 shows the results of FACS staining of A431 cells and CHO-S cells, using a culture supernatant of anti-EGFR antibody-producing cells.

FACS analysis was carried out by the following procedures. That is, A431 cells ($5 \times 10^6$ cells per sample) were recovered in a 1.5-mL tube, and were then washed with an FACS buffer once. Thereafter, the cells were suspended in the culture supernatant of each of the 55 clones prepared in the section 5 above, and the suspension was then left on ice for 20 minutes. Thereafter, the resultant cells were washed with an FACS buffer twice and were then suspended in an FITC-conjugated anti-chicken IgM antibody (BETHYL; used at 1000-fold dilution), and the obtained suspension was then left on ice for 20 minutes. Thereafter, the resultant cells were washed with an FACS buffer twice, and were then suspended in 400 μL of an FACS buffer containing 1 μg/mL propidium iodide. Thereafter, the suspension was subjected to FACS analysis. Among the culture supernatants of the used 55 clones, clone examples showing binding ability to the A431 cells are shown in FIG. 5. For the FACS analysis, Cell Lab Quanta SC MPL (Beckmann Coulter) was used, and as analysis software, Flowjo (Tree Star) was used. The results are shown in FIG. 5. The results of experiments using the culture supernatants of clone #33 and clone #11 are shown in FIGS. 5A and 5B, respectively. In addition, the results of an experiment using a commercially available anti-EGFR antibody are shown in FIG. 5C. From these results, it became clear that an antibody produced by clone #33 reacts with an EGFR molecule on the A431 cell under physiological conditions. The same results were obtained from the 52 other clones that were specific to EGFR. As a negative control, suspension CHO cells were used, instead of the A431 cells, and the same analysis as described above was carried out.

7. Production of Claudin2 Expression Vector and Production of Claudin2 Stably Expressing CHO Cells A sequence corresponding to the coding region of a human Claudin2 gene as a four-transmembrane protein was incorporated into the multicloning site of a pMClneo vector (Stratagene), so as to construct a Claudin2 expression vector, pMC-CL2.

CHO cells were transfected with this expression vector, and drug selection was then carried out using Geneticin (Invitrogen), so as to establish CLCN2/CHO as Claudin2 stably expressing CHO cells.

8. Selection Using Claudin2 Transiently Expressing CHO-S Cells

8-1. Removal of Unnecessary Antibody-Expressing DT40 from ADLib Library by Negative Selection $1 \times 10^7$ CHO-S cells were transfected with 2.5 μg of a pMACS4.1 plasmid serving as a CD4 expression vector, using Cell Line Nucleofector Kit V. This operation was repeated five times. Then, the cells were recovered and were then cultured in a CHO-S-SFM medium for 16 hours. Subsequently, mitomycin C (Nacalai Tesque, Inc.) was added in a final concentration of 10 μg/mL to the culture, and the obtained mixture was continuously cultured for further 3 hours. By the treatment with mitomycin C, while the expression of CD4 on the CHO-S cell membrane was maintained, the growth of the cells was suppressed.

After completion of the treatment with mitomycin C, the cells were recovered. Streptavidin-labeled Dynabeads ($5 \times 10^7$ beads; Veritas), on which a previously prepared biotin-labeled anti-CD4 mouse monoclonal antibody (BioLegend) had been immobilized, were allowed to react with CD4-expressing CHO-S cells ($1 \times 10^7$ living cells). A total amount ($1 \times 10^7$ cells) of the thus prepared Dynabeads-bound CD4-expressing CHO-S cells were suspended in and mixed with ADLib library cells ($1 \times 10^8$ cells), and while shaking, the mixture was incubated at 4° C. for 30 minutes, so that the CD4-expressing CHO-S cells were allowed to react with unnecessary antibody-expressing DT40 cells contained in the ADLib library. After completion of the reaction, the cell suspension was placed in a KingFisher Magnetic Particle Processor (Thermo Fisher Scientific), and complexes consisting of the Dynabeads used as magnetic beads and the cells were adsorbed on a magnet, thereby removing unnecessary antibody-expressing DT40 cells from the ADLib library (negative selection). The unadsorbed DT40 cell population was used as an ADLib library in positive selection as a next step.

8-2. Isolation of Anti-Claudin2 Antibody-Producing DT40 Cells by Positive Selection Using Cell Line Nucleofector Kit V, CHO-S cells ($1 \times 10^7$ cells) were co-transfected with 2.5 μg of a pMACS4.1 plasmid used as a CD4 expression vector and 2.5 μg of pMC-CL2 used as a Claudin2 expression vector. The cells were recovered and were then cultured in a CHO-S-SFM medium for 16 hours. Subsequently, mitomycin C (Nacalai Tesque, Inc.) was added in a final concentration of 10 μg/mL to the culture, and the obtained mixture was continuously cultured for further 3 hours. By the treatment with mitomycin C, while the expression of CD4 and Claudin2 on the CHO-S cell membrane was maintained, the growth of the cells was suppressed.

After completion of the treatment with mitomycin C, the cells were recovered. Streptavidin-labeled Dynabeads ($5 \times 10^6$ beads; Veritas), on which a previously prepared biotin-labeled anti-CD4 mouse monoclonal antibody (BioLegend) had been immobilized, were allowed to react with CD4 and Claudin2 co-expressing CHO-S cells ($1 \times 10^6$ living cells). A total amount ($1 \times 10^6$ cells) of the thus prepared Dynabeads-bound CD4 and Claudin2 co-expressing CHO-S cells were suspended in and mixed with an ADLib library (approximately $1 \times 10^8$ cells), on which the above-described negative selection had been performed. While shaking, the mixture was incubated at 4° C. for 30 minutes, so that the CD4 and Claudin2 co-expressing CHO-S cells were allowed to react with the ADLib library.

After completion of the reaction, the cell suspension was placed in a KingFisher Magnetic Particle Processor (Thermo Fisher Scientific), and complexes consisting of the Dynabeads used as magnetic beads and the cells were adsorbed on a magnet and removed. This operation was repeated in a washing solution, so that non-specifically reacting DT40 cells were removed by washing. A total amount of the cells recovered after the washing operation were plated on two 96-well plates, and approximately 10 days later, the culture supernatant was recovered. The presence of an anti-Claudin2 antibody in the culture supernatant was examined by cell ELISA.

Figure 6:
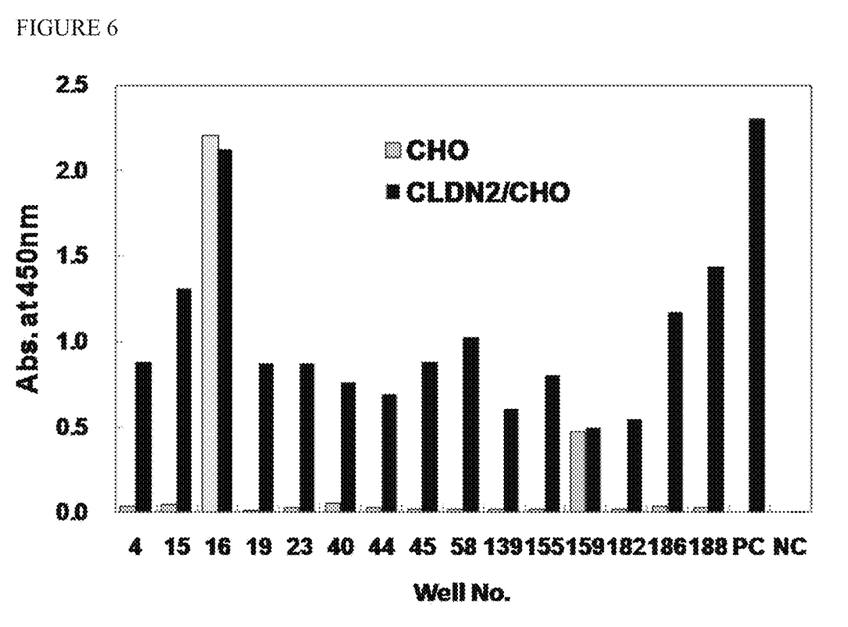
FIG. 6 shows the results obtained by examining the reactivity of a culture supernatant of anti-Claudin2 antibody-producing cells with Claudin2-expressing CHO cells and untreated CHO cells according to Cell ELISA.

Cell ELISA was carried out according to the following method. There was prepared a plate, on which CLDN2/CHO serving as Claudin2 stably expressing cells or untreated CHO cells were plated in a concentration of $3 \times 10^4$ cells/well, and the cells were then cultured at 37° C. in 5% $CO_2$ for 2 days. After the culture supernatant had been removed from this plate, 100 μL of a cell culture supernatant after positive selection was added thereto, and it was then reacted at room temperature for 1 hour. The wells were washed with PBS containing 0.05% Tween 20, and thereafter, 100 μL of 10.000-fold diluted anti-chicken IgM-HRP (BETHYL) was reacted as a secondary antibody with the resultant. The reaction product was washed with PBS containing 0.05% Tween20, and 100 μL of TMB+(Dako) was then added thereto as a coloring solution, followed by incubation for 30 minutes. Thereafter, the reaction was terminated by addition of 100 μL of 1 N sulfuric acid, and the absorbance at 450 nm was then measured, so as to examine the presence of an anti-Claudin2 antibody in the cell culture supernatant recovered by positive selection. The two 96-well plates, on which the cells after completion of the positive selection had been plated, were examined. As a result, as shown in FIG. 6, wells, which did not react with unreacted CHO cells but specifically reacted with CLDN2/CHO as Claudin2 stably expressing cells, were found at high rates. In the figure, PC indicates an antibody established by ADLib selection using, as an antigen, a synthetic peptide corresponding to one of extracellular loops of Claudin2. This PC was used as a positive control. On the other hand, NC indicates an antibody directed against streptavidin, which was established by ADLib selection. This NC was used as a negative control.

As stated above, it was demonstrated that the present invention can be applied to production of, not only an antibody directed against EGFR as a one-transmembrane protein, but also an antibody directed against a four-transmembrane protein, wherein such antibody has been hardly produced so far.

INDUSTRIAL APPLICABILITY

The present invention enables production of a desired antibody directed against a transmembrane protein, which has been hardly obtained so far, and it is also able to enhance the probability of obtaining what is called a functional antibody that has effects on the functions of the transmembrane protein. Accordingly, the method of the present invention can be widely used in the field of production of antibody pharmaceutical agents, antibody diagnostic agents, etc., or as a tool for research.

The invention claimed is:

1. A method, which comprises treating CHO-S cells that express a target antigen protein with mytomycin C so as to suppress cell growth but maintain expression of said target antigen protein, allowing an antibody library which is a cell population comprising cells that present an antibody on surfaces thereof, to come into contact with said CHO-S cells and isolating the cells, so as to separate a constituent member of the antibody library that forms a complex with said target antigen protein, wherein said target antigen protein is a multiple transmembrane protein.

2. The method according to claim 1, wherein the method of isolating the cells that express said target antigen protein on the surfaces thereof utilizes the bond between a marker antigen that is present on the cell surface, other than said the target antigen protein expressed on the cell surface, and an antibody directed against the marker antigen.

3. The method according to claim 2, wherein the marker antigen is a foreign protein.

4. The method according to claim 3, wherein said target antigen protein is a foreign protein.

5. The method according to claim 1, wherein the antibody library is a cell population comprising DT40 cells that present an antibody on the surfaces thereof.

6. A method comprising:
providing an antibody library which is a cell population comprising cells that present antibodies on surfaces thereof;
providing CHO-S cells that express target antigen protein, wherein said target antigen protein is a multiple transmembrane protein and is expressed in a physiological state on a cell membrane thereof;
treating said CHO-S cells with mytomycin C so as to suppress cell growth but maintain expression of said target antigen protein;
allowing said antibody library to come into contact with said CHO-S cells; and
isolating the cells so as to separate a constituent member of the antibody library that forms a complex with said multiple transmembrane protein expressed in the physiological state.

7. A method comprising:
providing CHO-S cells that express a target antigen protein, wherein said target antigen protein is a multiple transmembrane protein;
treating said CHO-S cells with mytomycin C so as to suppress cell growth but maintain expression of said target antigen protein;
providing an antibody cell library which is a cell population comprising cells that present antibodies on surfaces thereof;
allowing said antibody cell library to come into contact with said CHO-S cells; and
isolating the cells so as to separate a constituent member of the antibody cell library that forms a complex with the target antigen protein.

8. The method according to claim 7, wherein said CHO-S cells include a marker protein, and including magnetic beads that can bind said marker protein, wherein said isolating step uses magnetism to obtain said complexes including said magnetic beads bound to said marker protein.

9. The method according to claim 7, wherein the antibody cell library is a cell population comprising DT40 cells that present antibodies on the surfaces thereof.

10. The method of claim 7 wherein said multiple transmembrane protein is expressed in a physiological state on a cell membrane of said CHO-S cells.

11. The method of claim 7 wherein said target antigen protein is selected from the group consisting of growth factor receptor proteins, four-transmembrane proteins and seven-transmembrane proteins.

12. The method of claim 7 wherein said target antigen protein is selected from the group consisting of EGFR, IGF-1R, CD81, CXCR4, Claudin2 and sphingolipid receptors.

13. A method comprising:
  providing target antigen expressing cells that express a target antigen protein, wherein said target antigen protein is a multiple transmembrane protein, wherein the target antigen expressing cells are capable of presenting the target antigen protein on the surface thereof after the target antigen protein has been expressed therein, and the target antigen expressing cells are human-derived cells in which physiological post-translational modification or intracellular localization is likely to be provoked;
  treating the target antigen expressing cells with mytomycin C and culturing the target antigen expressing cells, so as to suppress cell growth but maintain expression of said target antigen protein;
  providing an antibody cell library which is a cell population comprising cells that present antibodies on surfaces thereof;
  allowing said antibody cell library to come into contact with the target antigen expressing cells; and
  isolating the cells so as to separate a constituent member of the antibody cell library that forms a complex with the target antigen protein.

14. The method of claim 13 wherein said target antigen protein is selected from the group consisting of growth factor receptor proteins, four-transmembrane proteins and seven-transmembrane proteins.

15. The method of claim 13 wherein said target antigen protein is selected from the group consisting of EGFR, IGF-1R, CD81, CXCR4, Claudin2 and sphingolipid receptors.

* * * * *

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial
<220> FEATURE:
<223> OTHER INFORMATION: Synthetic nucleotides

<400> SEQUENCE: 1
ttgctagccc agtattgatc gggagagc                                        28

<210> SEQ ID NO 2
<211> LENGTH: 20
<212> TYPE: DNA
<213> ORGANISM: Artificial
<220> FEATURE:
<223> OTHER INFORMATION: Synthetic nucleotides

<400> SEQUENCE: 2
caggctcggt catgtgttta                                                 20

<210> SEQ ID NO 3
<211> LENGTH: 20
<212> TYPE: DNA
<213> ORGANISM: Artificial
<220> FEATURE:
<223> OTHER INFORMATION: Synthetic nucleotides

<400> SEQUENCE: 3
gcacctgtaa aatgccctgt                                                 20

<210> SEQ ID NO 4
<211> LENGTH: 25
<212> TYPE: DNA
<213> ORGANISM: Artificial
<220> FEATURE:
<223> OTHER INFORMATION: Synthetic nucleotides
```

-continued

```
<400> SEQUENCE: 4
gcccatgaga aatttacagg aaatc                                         25

<210> SEQ ID NO 5
<211> LENGTH: 23
<212> TYPE: DNA
<213> ORGANISM: Artificial
<220> FEATURE:
<223> OTHER INFORMATION: Synthetic nucleotides

<400> SEQUENCE: 5
cagcttggat cacactttg gca                                            23

<210> SEQ ID NO 6
<211> LENGTH: 25
<212> TYPE: DNA
<213> ORGANISM: Artificial
<220> FEATURE:
<223> OTHER INFORMATION: Synthetic nucleotides

<400> SEQUENCE: 6
gcccatgaga aatttacagg aaatc                                         25

<210> SEQ ID NO 7
<211> LENGTH: 23
<212> TYPE: DNA
<213> ORGANISM: Artificial
<220> FEATURE:
<223> OTHER INFORMATION: Synthetic nucleotides

<400> SEQUENCE: 7
cagcttggat cacactttg gca                                            23
```